(12) United States Patent  (10) Patent No.: US 7,333,203 B2
Ott  (45) Date of Patent: Feb. 19, 2008

(54) DEVICE FOR SCANNING A YARN WITH A LIGHT BEAM

(75) Inventor: Philipp Ott, Wernetshausen (CH)

(73) Assignee: Uster Technologies AG, Uster (CH)

( * ) Notice: Subject to any disclaimer, the term of this patent is extended or adjusted under 35 U.S.C. 154(b) by 265 days.

(21) Appl. No.: 10/534,247

(22) PCT Filed: Nov. 6, 2003

(86) PCT No.: PCT/CH03/00727

§ 371 (c)(1),
(2), (4) Date: Oct. 13, 2005

(87) PCT Pub. No.: WO2004/044579

PCT Pub. Date: May 27, 2004

(65) Prior Publication Data

US 2006/0164646 A1    Jul. 27, 2006

(30) Foreign Application Priority Data

Nov. 13, 2002  (CH)  .................................. 1901/02

(51) Int. Cl.
*G01N 21/84* (2006.01)
(52) U.S. Cl. ................................... 356/430
(58) Field of Classification Search .................. None
See application file for complete search history.

(56) References Cited

U.S. PATENT DOCUMENTS 5,414,520 A   5/1995  Joss et al.
6,346,819 B1  2/2002  Joss et al.
6,771,365 B1  8/2004  Pirani et al.
6,798,506 B2  9/2004  Furter

FOREIGN PATENT DOCUMENTS

| DE | 199 55 292 | 5/2001 |
| EP | 0 399 945 | 11/1990 |
| EP | 0 761 585 | 3/1997 |
| EP | 1 018 645 | 7/2000 |

OTHER PUBLICATIONS

U.S. Appl. No. 10/482,295, filed Dec. 23, 2004, Sharony.
U.S. Appl. No. 09/806,439, filed Mar. 30, 2001, Parani.

*Primary Examiner*—Gregory J Toatley, Jr.
*Assistant Examiner*—Amanda H Merlino
(74) *Attorney, Agent, or Firm*—Buchanan Ingersoll & Rooney PC

(57) ABSTRACT

The invention relates to a device for scanning a thread, which is displaceable in the longitudinal direction thereof inside a measuring slot, by means of an optical beam emitted by a light source. The device includes a receiver of light reflected on the thread and a unit for processing electrical signals received by the receiver. The aim of the invention is to develop a small-sized device which is easy to operate and which makes it possible to detect foreign matter contained in the thread in a most selective manner at a high sensitivity. For this purpose, the light emission in at least two wavelength ranges is carried out by means of a light source, with these wavelength ranges being determined by two main wavelengths.

6 Claims, 4 Drawing Sheets

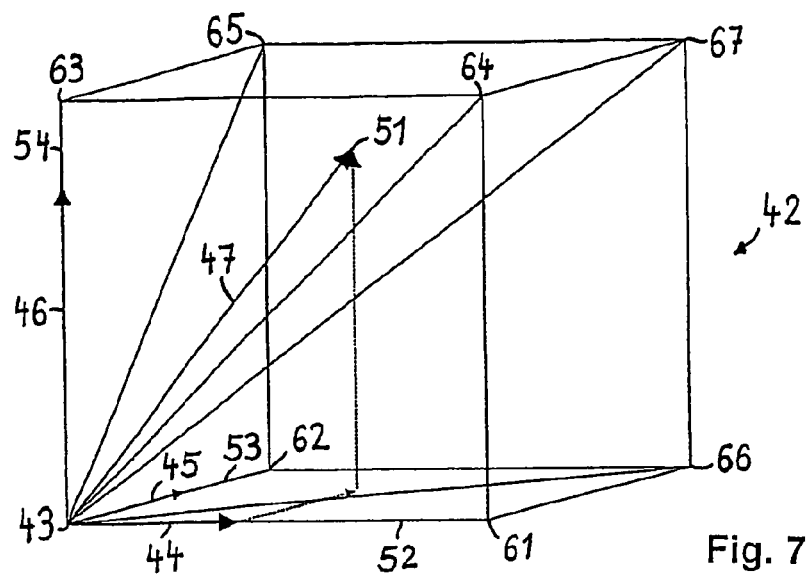
Fig. 7
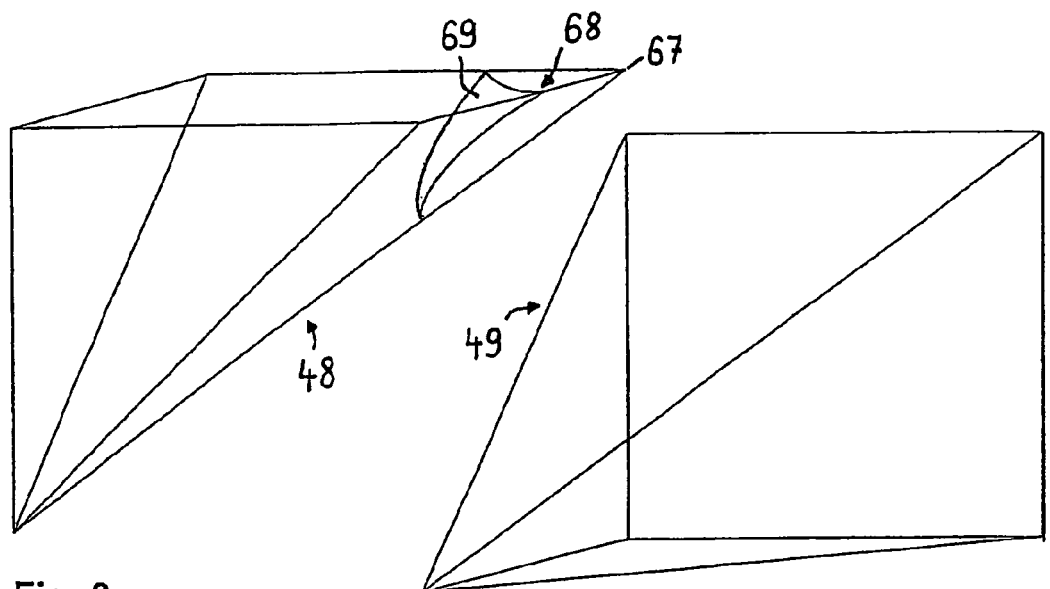
Fig. 8
Fig. 9
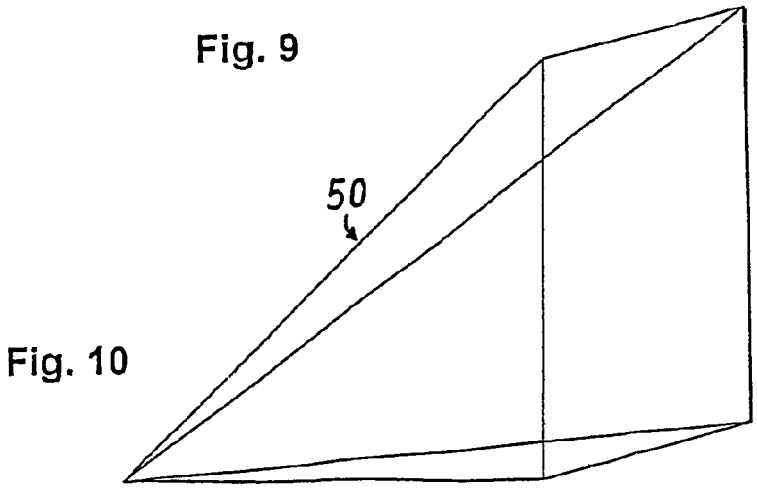
Fig. 10

DEVICE FOR SCANNING A YARN WITH A LIGHT BEAM

This disclosure is based upon German Application No. 1901/02, filed Nov. 13, 2002, and International Application No. PCT/CH2003/000727, filed Nov. 6, 2003, the contents of which are incorporated herein by reference.

BACKGROUND OF THE INVENTION

The invention relates to a device for scanning a yarn that is moved in its longitudinal direction in a measuring gap with a light beam from a light source, which device has a receiver for light reflected by the yarn and a unit for processing electrical signals from the receiver.

Such a device is known, for example, from EP 0 761 585, in which there is provided a light source which emits light which on the one hand is reflected and on the other hand is also shaded by the yarn. The light received by receivers is converted in a manner known per se into electrical signals for which ranges or threshold values can be provided in order, for example, to detect foreign bodies in the yarn.

This device has the disadvantage that, for example, foreign bodies in the yarn that have the same colour as the emitted light cannot be detected therewith. However, the same is also true, for example, of transparent foreign bodies such as pieces of plastics film in the yarn, so that such foreign bodies cannot be detected with this device.

A further device of this type is known from WO 95/29396, in which three different light sources are associated with a receiver for white light. These three light sources are in the form of three light-emitting diodes, each diode emitting light of a different main wavelength in the visible range. When viewed in the longitudinal direction of the yarn, the light sources are arranged one behind the other next to the yarn and are so oriented that they illuminate the yarn and a background that is located behind the yarn and absorbs as much light as possible. The signals produced in the receiver by reflection of the light by the yarn are processed in such a manner that ratios are formed from the values determined for the signals in the individual main wavelengths, which ratios can in turn be measured against criteria.

A particular disadvantage of this device is that it is only suitable for the evaluation of reflected light with yarn in front of a preferably black background. Moreover, the arrangement of three or more diodes at intervals along the yarn requires a large amount of space, which may not even be available at those locations in textile machines that are intended for such devices. This device has the additional problem that operation of the individual light sources must take into account the movement of the yarn and it must therefore be provided that the same point on the yarn is always illuminated with light of a different colour.

SUMMARY OF THE INVENTION

The invention, as characterised in the patent claims, achieves the object of providing a device of the mentioned type which requires little space, is more simple to operate and permits the detection of foreign bodies in the yarn more selectively and with greater sensitivity.

This is achieved according to the invention with a device which provides a single light source for emitting light in at least two wavelength regions, the wavelength regions being determined by main wavelengths. The main wavelengths determine at least two colours in the region of wavelengths of visible light. These are preferably the colours red, green or blue. The light source is preferably in the form of a light-emitting diode which is able separately to emit visible light in three colours in the visible range. The light source and the receiver exhibit principal axes for the emission and reception of light which together define a plane that is transverse to the longitudinal direction of the yarn. The unit for processing electrical signals from the receiver for reflected light forms a vector in a plane or in a space from the signals in each of the at least two specified wavelength regions and forms a sum vector from the vectors for the various signals. For the end point of the sum vector in the space there is specified a region which indicates whether the electrical signal from the receiver processed to form the sum vector indicates a foreign body in the yarn. The space in which the vectors are calculated and/or represented preferably forms a cube with axes along which values for the intensity of three main wavelengths are plotted.

The advantages achieved by the invention are that the single light source illuminates the yarn with light having different wavelengths from virtually the same point, so that the light beams in all the wavelength regions strike the yarn within a narrowly limited angle. This light source does not require much space either, so that it is possible to build a measuring head for yarn that can be installed at a narrowly delimited location in the spinning machine or spooler. Moreover, the mentioned light source is substantially less expensive than a group having one light source for each colour. Because it is also possible to provide a plurality of receivers which convey the light reflected by the yarn to a unit for processing electrical signals which processes these signals in exactly the same manner, it is possible to scan the whole of the yarn surface facing the receivers. The use of a plurality of identical receivers for white light permits the detection of the colours of the yarn without spectral errors. The evaluation of the resulting signals, with the aim of forming a sum vector from the portions of the individual colours, makes possible the selective detection of foreign bodies of particular colours and colour shades corresponding to particular materials. However, it is also possible to deliberately leave foreign bodies in the yarn, by first detecting them or by specifying a region for the end point of the sum vector so that certain foreign bodies are not detected at all. By the targeted cleaning of the yarn in respect of particular impurities or foreign bodies, the performance of the production machines can be substantially improved.

BRIEF DESCRIPTION OF THE DRAWINGS

The invention is explained in greater detail hereinbelow by means of an example and with reference to the accompanying figures, in which.

DETAILED DESCRIPTION

Figure 1:
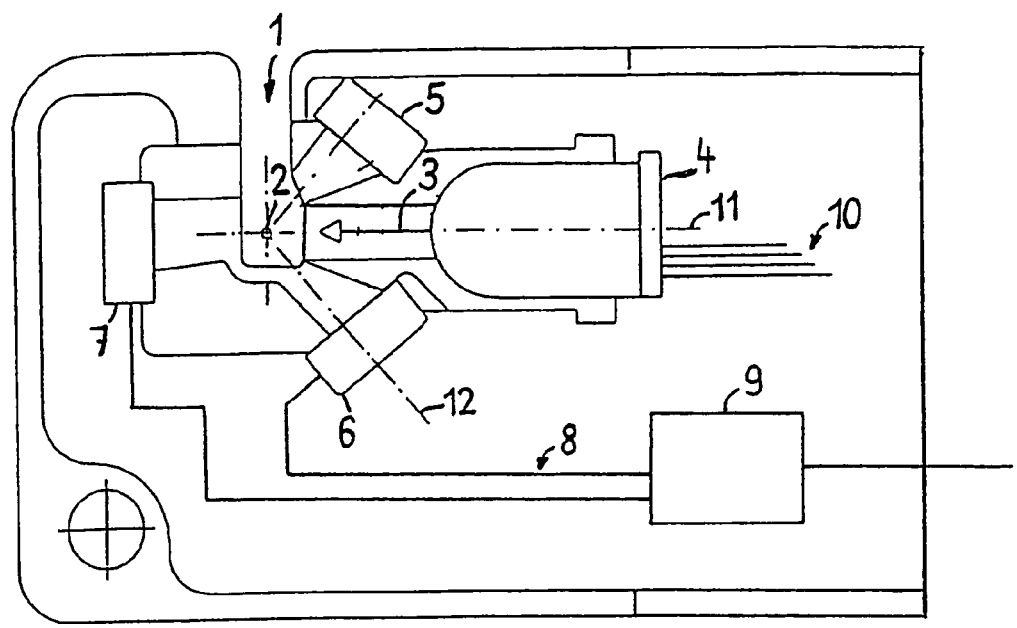
FIG. 1 shows a section through a device according to the invention.

FIG. 1 shows a device according to the invention, such as, for example, a measuring head for measuring yarn properties or for a yarn cleaner, having a measuring gap 1 in which a yarn 2 is moved in its longitudinal direction, the longitudinal direction here being oriented approximately perpendicularly to the drawing plane. A light beam 3 is produced by a light source 4 and is directed towards the yarn 2. Receivers 5 and 6 for light reflected by the surface of the yarn are provided. The light source provided is a light-emitting diode, for example a so-called RGB-LED, as produced by Nichia (viewable on the Internet at www.nichia.co.jp) of type NTSM 515. However, it is also conceivable to use other light sources, for example based on a laser. A further receiver 7 can additionally be provided for light shaded by the yarn 2. The receiver(s) 5, 6, 7 is/are each connected by way of a line or a bus 8 to a unit 9 for processing electrical signals from the receiver(s). The unit 9 consists of a computer with a memory, that is to say, for example, of a microprocessor of known type. The light source 4 has four connections 10 via which the individual wavelength regions or colours can be operated individually. In this example, the single light source 4 and the receiver 6 have principal axes 11 and 12 for the emission and reception of light which together define a plane that is transverse to the longitudinal direction of the yarn and here corresponds to the drawing plane.

Figure 2:
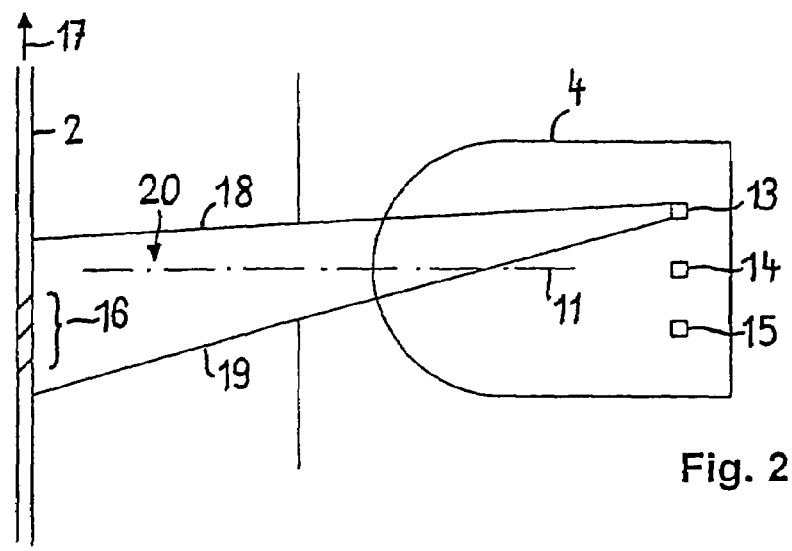
FIGS. 2, 3 and 4 each show a diagrammatic representation of part of the device in different phases.

FIG. 2 shows, in a simplified representation, the light source 4 with three light-emitting diodes 13, 14 and 15, and the yarn 2 with a foreign body 16 embedded therein. Relative to the principal axis 11 of the light source 4, the foreign body is located just before the principal axis, starting from a direction of movement indicated by an arrow 17. The yarn 2 with the foreign body 16 is here illuminated, for example, by red light from the diode 13, which emits light in a region 20 as delimited by lines 18 and 19.

Figure 3:
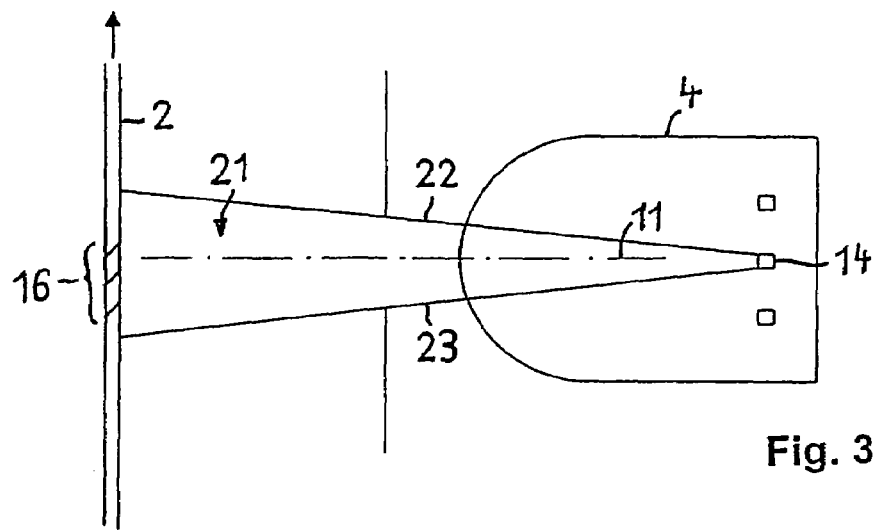

FIG. 3 shows a representation according to FIG. 2 wherein the yarn 2 with the foreign body 16 is located approximately at the principal axis 11. The yarn 2 with the foreign body 16 is here illuminated, for example, by green light from the diode 14, which emits light in a region 21 as delimited by lines 22 and 23.

Figure 4:
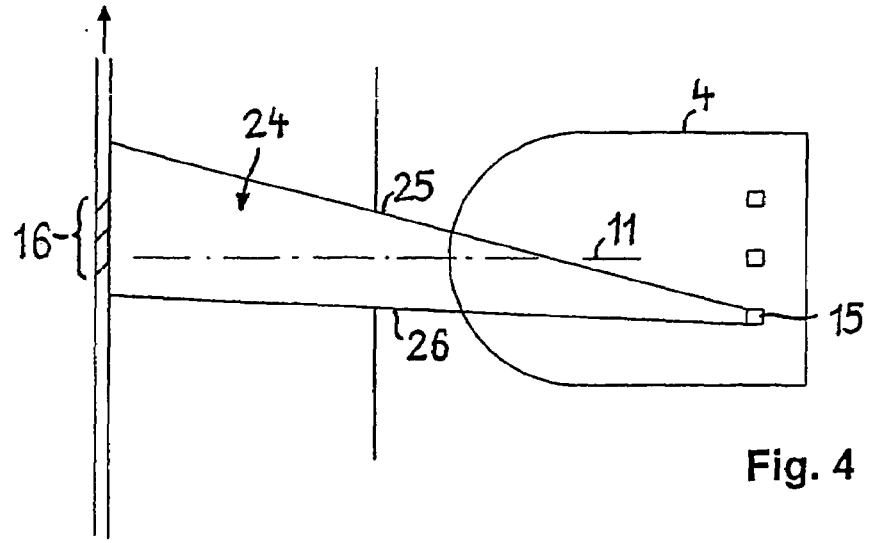

FIG. 4 shows a representation according to FIG. 2 wherein the yarn 2 with the foreign body 16 is located above the principal axis 11. The yarn 2 with the foreign body 16 is here illuminated, for example, by blue light from the diode 15, which emits light in a region 24 as delimited by lines 25 and 26.

Figure 5:
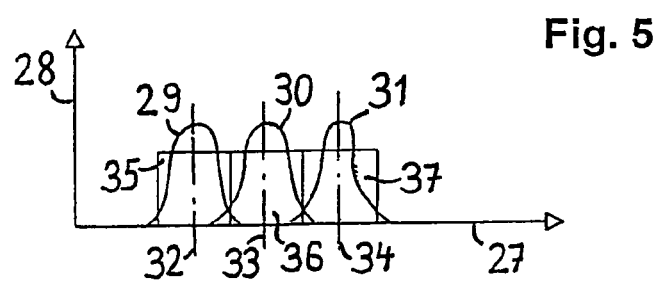
FIG. 5 shows a diagrammatic representation of wavelength regions, FIGS. 6 and 7 each show a diagrammatic representation of the evaluation of the measured signals, FIG. 8 to 10 each show a representation of a target region for the evaluation, and FIGS. 11 and 12 each show representations of possible ways of operating the light source of the device.

FIG. 5 shows a representation of different wavelength regions over an axis 27, along which values for wavelengths can be plotted. Values for the intensity of a signal as a function of the wavelength can be plotted along an axis 28. Three wavelength regions 29, 30 and 31 are recorded here by way of example by means of curves which indicate the progression of the intensity of the emitted light in the region of their three main wavelengths 32, 33 and 34. For the sake of simplicity and for subsequent representations, these wavelength regions can also be represented by simple rectangles 35, 36 and 37.

Figure 6:
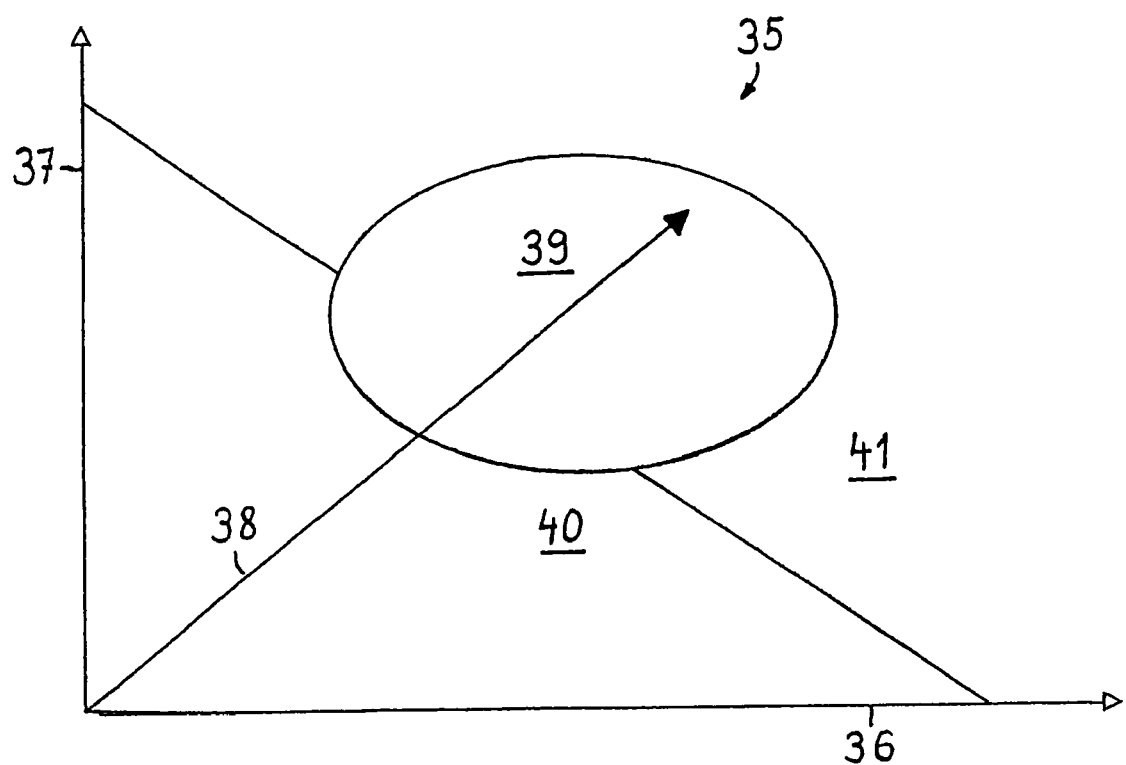

FIG. 6 shows a plane 35 defined by axes 36 and 37. Along these axes 36, 37, values for the intensity of in each case one colour of the light from the light source 4 reflected by the yarn can be plotted as vectors. A sum vector 38 can be calculated therefrom. In the plane 35, regions 39, 40, 41 representing particular properties of the yarn can be specified. Such properties may be the nature of the base materials of which the yarn consists or the nature of the foreign bodies occurring in the yarn.

Analogously to FIG. 6, which applies to light from two different wavelength regions, FIG. 7 shows a space 42, delimited as a cube, for the representation of vectors which correspond to the intensity of the received signals in three different wavelength regions. One corner 43 of the space should here serve as the starting point for vectors 44, 45, 46, each of which represents a particular wavelength region. 47 denotes a sum vector composed of the three vectors 44, 45 and 46. This space or cube 42 can be divided into different regions. One such region 48 is shown in FIG. 8, one region 49 is shown in FIG. 9 and one region 50 is shown in FIG. 10. These regions 48, 49 and 50 are intended as the target region for the end point 51 of the sum vector 47. Depending on whether the end point 51 lies in one of these regions 48, 49, 50 or not, a particular condition for a property of the yarn, such as, for example, the presence of a particular foreign body, is or is not met. The space 42, which here is in the form of a cube, is formed by axes 52, 53 and 54, along which values for the intensity of three main wavelengths are plotted.

Figure 11:
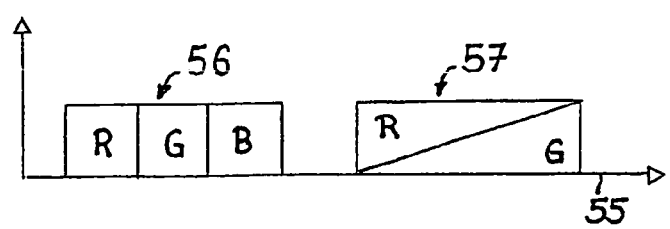

FIG. 11 shows various wavelength regions, as known from FIG. 5, in this case plotted over a time axis 55. This gives examples of possible repeating sequences for the emission of light by the light source 4. According to a sequence 56, the light source 4 is to emit light of the colours red, green and blue in succession. A sequence 57 indicates that, over a specified time, red-coloured light is to be emitted with decreasing intensity and at the same time green-coloured light is to be emitted with increasing intensity. If three colours are used, two or three sequences with in each case two colours are obtained. When the three sequences are complete, the first sequence 57 is begun again.

Figure 12:
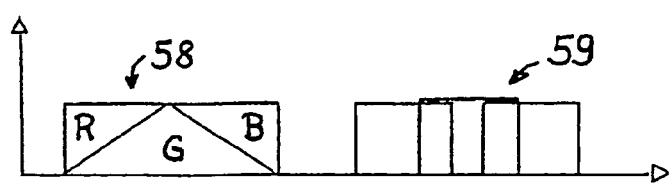

FIG. 12 shows further sequences analogous to FIG. 11. A sequence 58 for three colours which overlap but together give a specified overall intensity. A sequence 59 again involves three colours which are designated R, G and B and which overlap. The intensity of the signals in the three colours is always constant or maximum.

The mode of operation of the device is additionally to be described hereinbelow, in so far as it is not already evident from the above descriptive parts. In order to detect, for example, a particular foreign body in or another property of the yarn 2, the light source is operated by way of the connections 10 in such a manner, for example, that it emits light in only a limited wavelength region. This light is reflected by the yarn and thrown back to a receiver 5, 6, which receives the light and converts it into an electrical signal which is passed by way of the line or the bus 8 to the unit 9, which stores the signal or a numerical value derived therefrom. Immediately thereafter, the light source 4 is so operated that it emits light in a further wavelength region etc., so that a further signal or a further value can finally be stored in the unit 9. From the stored values, vectors 44, 45 and, optionally, 46 are formed in the computer of the unit 9, and a sum vector 38 or 47 is finally formed therefrom. Values that define at least one region 39, 40, 41 or 48, 49, 50 in the plane 35 or in the space 42 are stored in the unit 9, so that it is possible, by making a comparison, to determine whether the end point of the sum vector lies in one of these regions or not. As a result of such a comparison, a signal can then be emitted by the unit 9 by way of a line 60, which signal indicates whether, for example, a desired property is present, for example whether a foreign body is present in the yarn or not.

If a further receiver 7 for transmitted light is present, that receiver may, for example, emit a further signal to the unit 9 indicating the diameter of the yarn. It is thus also possible, in a known manner, to compensate for the effect of the diameter of the yarn on the reflected light received.

As already shown in FIGS. 11 and 12, there are various possible ways of operating the light source 4. If, for example, continuous transitions between two or more wavelength regions are used, as shown in sequences 57 and 58, it is then also possible to determine the vectors and the sum vector 38, 47 at different times during the sequence. The sum vector 38, 47 accordingly carries out a movement in the plane or in the space during the sequence and it is possible to determine at which times, or in which parts of the wavelength regions, the end point lies within a particular region 22. Starting from mixed light from two wavelength regions it is thus also possible to acquire information about properties of the yarn which are otherwise not obtainable.

For the separate illumination of the yarn according to a sequence 56, the cycle frequency with which the individual diodes 13, 14, 15 of the light source 4 are to be operated should be at least so great that the distance moved by a particular point, such as, for example, the location at which a foreign body 16 is embedded in the yarn 2, in a particular time is such that the point still falls within the regions 20, 21 and 24. That particular time here lasts three cycles or a multiple thereof. Because the diodes 13 to 15 are arranged extremely close to one another in the single light source 4, the time required for illumination with three wavelength regions is very short and it is accordingly readily possible to scan such a point three times while it is located in front of the light source 4.

If the colours red, green and blue are chosen as the wavelength regions, these and further colours can be recognised, in the representation according to FIG. 7, in the following arrangement in the space 42:

The intensity of the black colour should be maximum in corner 43. The intensity of the red colour should be maximum in corner 61. The intensity of the green colour should be maximum in corner 62. The intensity of the blue colour should be maximum in corner 63. The intensity of the colour magenta should be maximum in corner 64. The intensity of the colour cyan should be maximum in corner 65. The intensity of the colour yellow should be maximum in corner 66, and the intensity of the white colour should be maximum in corner 67.

It is known per se which formulae can be used to calculate the mentioned vectors. For the sake of completeness, an example is given here. The following applies to the length of the sum vector 47, as is known from FIG. 7 and which is here denoted $V_{47}$:

$$|V_{47}| = \sqrt{|V_{44}|^2 + |V_{45}|^2 + |V_{46}|^2}$$

wherein $V_{44}$, $V_{45}$ and $V_{46}$ denote the lengths of the vectors 44, 45 and 46. The direction of the sum vector is determined by known rules of trigonometry. An appropriately adapted calculation can be used for the vectors of FIG. 6.

The position of the sum vector 38, 47 can give an indication, for example, of whether a foreign body is present, what type it is and whether it is troublesome and must be removed or not. For example, it is possible according to FIG. 6 to determine that, for tolerated foreign bodies, the sum vector 38 in FIG. 6 should lie only with its end point in the region 41 or even in the region 39. In FIGS. 7 to 10 it could be assumed, for example, that the end point 51 of the sum vector 47 should lie in a region 68 delimited by an area 69 and close to the corner 67 when no foreign body is present and the yarn is white or almost white. If the end point 51 lies in the regions 48, 49 or 50, it is assumed that the foreign body is predominantly blue, green or red. However, such a foreign body may nevertheless be tolerable per se. This may be the case, for example, for a red foreign body when the yarn is subsequently to be dyed red.

The invention claimed is:

1. Device for scanning a yarn that is moved in its longitudinal direction in a measuring gap with a light beam from a light source, comprising a receiver for light reflected at the yarn, a unit for processing electrical signals from the receiver, and a single light source for emitting light in at least two wavelength regions, the wavelength regions being determined by two main wavelengths, said unit for processing electrical signals from the receiver including a computer which forms a vector from the values for each of the at least two specified wavelength regions and forms a sum vector from the vectors, wherein for the end point of the sum vector in a space a region is delimited which indicates whether the electrical signal from the receiver processed to form the sum vector indicates a foreign body in the yarn.

2. Device according to claim 1, wherein the main wavelengths determine two colours in the region of wavelengths of visible light.

3. Device according to claim 2, wherein the main wavelengths relate to the colours red, green and blue.

4. Device according to claim 1, wherein the single light source is in the form of a light-emitting diode which is able separately to emit visible light in three colours in the visible range.

5. Device according to claim 1, wherein the single light source and a receiver have principal axes for the emission and reception of light which together span a plane that is transverse to the longitudinal direction of the yarn.

6. Device according to claim 1, wherein the space forms a cube which is formed by axes along which values for the intensity of three main wavelengths are plotted.

* * * * *